United States Patent
Weaver et al.

[11] Patent Number: 6,140,517
[45] Date of Patent: Oct. 31, 2000

[54] ANTHRAQUINONE POLYSULFONAMIDE COLORANTS

[75] Inventors: Max Allen Weaver; James John Krutak, Sr., both of Kingsport; Clarence Alvin Coates, Jr., Blountville; Gerry Foust Rhodes, Piney Flats; Brian Edison Maxwell, Johnson City, all of Tenn.

[73] Assignee: Eastman Chemical Company, Kingsport, Tenn.

[21] Appl. No.: 08/906,642

[22] Filed: Aug. 7, 1997

Related U.S. Application Data

[60] Provisional application No. 60/025,366, Sep. 3, 1996.

[51] Int. Cl.[7] .................. C07C 311/37; C07C 303/38; C09B 69/10
[52] U.S. Cl. .................. 552/218; 8/404; 8/647; 8/676; 544/357; 552/219
[58] Field of Search .................. 552/218, 219; 544/357; 8/404, 647, 676

[56] References Cited

U.S. PATENT DOCUMENTS

| | | | |
|---|---|---|---|
| 2,731,476 | 1/1956 | Peter et al. | 260/371 |
| 2,994,693 | 8/1961 | Blake et al. | 260/144 |
| 3,299,103 | 1/1967 | Maier | 260/373 |
| 3,403,200 | 9/1968 | Randall | 260/857 |
| 4,403,092 | 9/1983 | Davis et al. | 528/290 |
| 4,778,742 | 10/1988 | Ong et al. | |
| 5,032,670 | 7/1991 | Parham et al. | 528/220 |
| 5,080,764 | 1/1992 | Kester et al. | 204/831 |
| 5,106,942 | 4/1992 | Krutak et al. | 528/272 |
| 5,453,482 | 9/1995 | Weaver et al. | 528/172 |

FOREIGN PATENT DOCUMENTS

| | | |
|---|---|---|
| 0 371 782 | 6/1990 | European Pat. Off. . |
| 727 996 | 4/1955 | United Kingdom . |
| 92/07913 | 5/1992 | WIPO . |
| 92/13921 | 8/1992 | WIPO . |
| 95 21958 | 8/1995 | WIPO . |

OTHER PUBLICATIONS

N. Otha, Photographic Science and Engineering, vol. 15, No. 5, Sep.–Oct., 1971, pp. 399–415.

*Primary Examiner*—Peter O'Sullivan
*Attorney, Agent, or Firm*—Matthew W. Smith; Karen A. Harding; Harry J. Gwinnell

[57] ABSTRACT

The invention relates to anthraquinone polysulfonamide colorants derived from colored disulfonyl chlorides containing anthraquinone chromophores by reacting with various diamines. The anthraquinone polysulfonamide colorants are useful for coloring a wide variety of products such as plastics, fibers, films, cosmetics, skin creams or lotions, polishes, waxes, hair colorations, coatings, paints, inks, etc. and are particularly useful in end uses where sublimation, migration, extraction and exudation of presently used colorants are problems.

16 Claims, No Drawings

ANTHRAQUINONE POLYSULFONAMIDE COLORANTS

RELATED APPLICATION

This application is based upon and claims the priority of provisional application 60/025,366, filed Sep. 3, 1996.

BACKGROUND OF THE INVENTION

1. Field of the Invention

The present invention relates to polysulfonamide colorants which are useful as tints, toners, and colorants for a variety of applications where nonextractability of the colorant is important. Since the colorant moieties are incorporated into the polymer chain, the colorant is not leachable, sublimable or extractable and does not exude from the composition. The polysulfonamide colorants are useful in a wide variety of products such as plastics, fibers, films, cosmetics, skin creams or lotions, soaps, hair colorations, waxes, polishes, coatings, paints, toners for impactless printing, inks, and etc., which will be safe to humans since exposure to toxic dye molecules readily absorbed by the body is greatly minimized. Thus, the colorant compositions have utility in a wide variety of applications where toxicological concerns are evident. The colorants are particularly useful for imparting stable coloration to a wide variety of thermoplastic compositions including polyesters, polycarbonates, polyamides, cellulose esters, polyurethanes, polyolefins, etc. by conventional melt blending techniques.

Plastics, paints, printing inks, rubber, cosmetics, and similar materials are typically colored by organic pigments when superior brilliance and tinctorial strength are important. Toxicity considerations have presented chronic problems relative to the use of organic pigments since some have been shown to be potential carcinogens and to cause contact dermatitis.

Plastics are also colored by using color concentrates consisting of physical admixtures of polymers and colorants (usually solvent dyes). However, the use of such physical admixtures to color polymeric materials such as polyester, e.g., poly(ethylene terephthalate) and blends thereof, present a number of problems:

1. Colorant migration during drying of the colored polyester pellets.
2. Colorant migration during extrusion and colorant accumulation on dies which can cause shutdowns for clean-up. Such colorant migration and accumulation result in time consuming and difficult clean-up, particularly when a polymer of another color is subsequently processed on the same equipment.
3. Colorants may not mix well, for example, when using two or more color concentrates to obtain a particular shade.
4. Colorants may diffuse or exude during storage and use of the colored polymeric material.

The polysulfonamide colorants eliminate or minimize the aforementioned problems associated with the use of conventional dyes and pigments.

2. Description of the Prior Art

It is known to produce polyester color concentrates having colorants copolymerized therein and to use these for coloring various materials including thermoplastics (See U.S. Pat. No. 5,032,670; U.S. Pat. No. 5,106,942; WO 92/07913; WO 92/13921). The polycondensation reactions required to prepare these polymeric colorants require high temperature conditions (>250° C.) and continuous large scale processing to be cost effective. This is in contrast to the polysulfonamide colorants of this invention which can be prepared at relatively low temperatures (e.g., usually 100° C. or less) in batch processing equipment.

U.S. Pat. Nos. 2,994,693; 3,403,200; and 5,080,764 all disclose colored polysulfonamides. More particularly, U.S. Pat. No. 2,994,693 discloses polysulfonamides derived from colored diaminoanthraquinones and diacid halides such as diacid halides of carboxylic acids, bis-sulfonyl halides and bis-haloformates. In contrast to the colored polysulfonamides of our invention, which contain anthraquinone chromophores, the colors of the prior art polysulfonamides are greatly different from that of the starting diaminoanthraquinone monomers, thus making control of hue and shade difficult. In this invention, the colored anthraquinone monomer contains at least two sulfonyl halide groups which are isolated from the color producing system. Thus, no substantial shifts in color are experienced when the colored di-sulfonyl halides are reacted with the uncolored diamines.

SUMMARY OF THE INVENTION

The invention provides a polymeric colorant having the formula I:

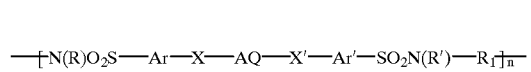

wherein:

AQ is a divalent anthraquinone radical which may be substituted with from 1 to 6 substituents, which may be the same or different and are selected from the group consisting of $C_1-C_8$ alkyl, $C_1-C_8$ alkoxy, $C_1-C_8$ alkanolyamino, aroylamino, $C_1-C_8$ alkylthio, amino, nitro, $C_1-C_8$ alkylamino, $C_3-C_8$ cycloalkylamino, $C_1-C_8$ alkanoyl, $C_1-C_8$ alkoxycarbonyl, trifluoromethlyl, cyano, $C_3-C_8$ cycloalkoxy, $C_3-C_8$ cycloalkyltio, heteroarylthio, $C_1-C_8$ alkylsulfonyl, arylsulfonyl, aroyl, carbamoyl, sulfamoyl, $C_1-C_8$ alkanoylamino, aroylamino, $C_1-C_8$ alkylsulfonamido, arylsulfonamido, arylthio, aryloxy, arylamino, and hydroxy groups;

X and X' are independently selected from the group consisting of Y, -Y-alkylene, -Y-(alkylene-Y'-)$_m$, -Y-alkylene-$C_3-C_8$-cycloalkylene, Y-$C_3-C_8$-cycloalkylene-Y', and Y-alkylene-$C_3-C_8$-cycloalkylene-alkylene-Y', wherein m is 1–3, and Y and Y' are independently —O—, —S—, —N(R)CO—, —N(R)SO$_2$—, or —N(R$_2$)—;

Ar and Ar' are independently a divalent benzene or naphthalene radical which may be substituted with from 1 to 4 substituents which may be the same or different and are selected from the group consisting of $C_1-C_8$ alkyl, $C_1-C_8$ alkoxy, $C_1-C_8$ alkanolyamino, aroylamino, $C_1-C_8$ alkylthio or halogen groups;

R and R' are independantly hydrogen, $C_1-C_8$ alkyl, $C_3-C_8$ cycloalkyl, heteroaryl or aryl;

$R_1$ is a divalent organic radical, with the proviso that when $R_1$ is ethylene, R and R' may be combined to represent an ethylene radical;

$R_2$ is selected from the group consisiting of hydrogen, $C_1-C_8$ alkyl, $C_3-C_8$ cycloalkyl, $C_1-C_8$ alkanoyl, aroyl, $C_1-C_8$ alkylsulfonyl, arylsulfonyl, carbamoyl, or sulfamoyl; and n is an integer of from about 3 to about 30.

The invention also provides a polymeric colorant comprising a unit of the formula I.

The invention further provides a process for preparing a polymeric colorant of the formula I which comprises reacting a dihalosulfonyl compound of the formula: $ZO_2S$—Ar—

X-AQ-X'—Ar'—SO₂Z with a diamine of the formula HN(R)—R₁—N(R')H, in a solvent which does not react with the dihalosulfonyl compound or the diamine, and in the presence of an acid acceptor, wherein Z is a halogen.

The invention still further provides a dihalosulfonyl compound of the formula ZO₂S—Ar—X-AQ-X'—Ar'—SO₂Z wherein Ar, Ar', X, X', and AQ are defined above and Z is fluorine.

DETAILED DESCRIPTION OF THE PREFERRED EMBODIMENT

The polysulfonamide colorants of the present invention correspond to Formula I:

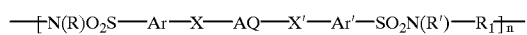

I wherein:

Ar and Ar' each independently represent a divalent radical of the benzene or naphthalene series; X and X' are independently selected from the group consisting of Y, -Y-alkylene, -Y-(alkylene-Y'-)$_m$, -Y-alkylene-C₃–C₈-cycloalkylene, Y-C₃–C₈-cycloalkylene-Y', Y-alkylene-C₃–C₈-cycloalkylene-alkylene-alkylene-Y', wherein m is 1–3, Y and Y' are independently selected from the group consisting of —O—, —S—, —N(R)CO—, —N(R)SO₂—, and —N(R₂)—, AQ is a divalent anthraquinone radical; R and R' are independently selected from the group consisting of hydrogen, $C_1$–$C_8$ alkyl, $C_3$–$C_8$ cycloalkyl, heteroaryl and aryl; R₁ is a divalent organic radical, with the proviso that when R₁ is ethylene, R and R' may be combined to represent an ethylene radical; and R₂ is selected from the group consisting of hydrogen, $C_1$–$C_8$ alkyl, $C_3$–$C_8$ cycloalkyl, $C_1$–$C_8$ alkanoyl, aroyl, $C_1$–$C_8$ alkylsulfonyl, arylsulfonyl, carbamoyl, and sulfamoyl; n is an integer of from about 3 to about 30, preferably an integer from about 5 to about 20.

Each divalent radical represented by Ar and Ar' may be further substituted with 1–4 substituents which may be the same or different and are selected from the group consisting of $C_1$–$C_8$ alkyl, $C_1$–$C_8$ alkoxy, $C_1$–$C_8$ alkanolyamino, aroylamino, $C_1$–$C_8$ alkylthio and halogen.

The divalent anthraquinone radical (AQ) may be further substituted with 1–6 substituents which may be the same or different and are selected from the group consisting of $C_1$–$C_8$ alkyl, $C_1$–$C_8$ alkoxy, $C_1$–$C_8$ alkanolyamino, aroylamino, $C_1$–$C_8$ alkylthio, halogen, amino, nitro, $C_1$–$C_8$ alkylamino, $C_3$–$C_8$ cycloalkylamino, $C_1$–$C_8$ alkanoyl, $C_1$–$C_8$ alkoxycarbonyl, trifluoromethyl, cyano, $C_3$–$C_8$ cycloalkoxy, $C_3$–$C_8$ cycloalkylthio, heteroarylthio, $C_1$–$C_8$ alkylsulfonyl, arylsulfonyl, aroyl, carbamoyl, sulfamoyl, aroylamino, $C_1$–$C_8$ alkylsulfonamido, arylsulfonamido, arylthio, aryloxy, arylamino and hydroxy.

The organic radical R₁ can be selected from a wide variety of divalent linking groups including, $C_2$–$C_{12}$ alkylene, $C_3$–$C_8$ cycloalkylene, —CH₂—$C_3$–$C_8$ cycloalkylene-CH₂—, carbocyclic and heterocyclic arylene and these in combination. The alkylene linking groups may contain within or attached to their main chain one or more hetero atoms, e.g., oxygen, sulfur, nitrogen, substituted nitrogen, and/or cyclic groups such as $C_3$–$C_8$ cycloalkylene, carbocyclic arylene, divalent aromatic heterocyclic groups or ester/amide groups such as

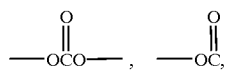

-continued

—OC—C₁–C₁₂alkylene-CO—,

—OC-arylene-CO—,

—OCNH—C₁–C₁₂alkylene-NHCO—,

—OCNH-arylene—NHCO—, —NHCNH—,

—NHC—, and

—NHC—C₁–C₁₂alkylene-CNH—.

Examples of $C_2$–$C_{12}$ alkylene radicals containing cyclic moieties in the alkylene chain include:

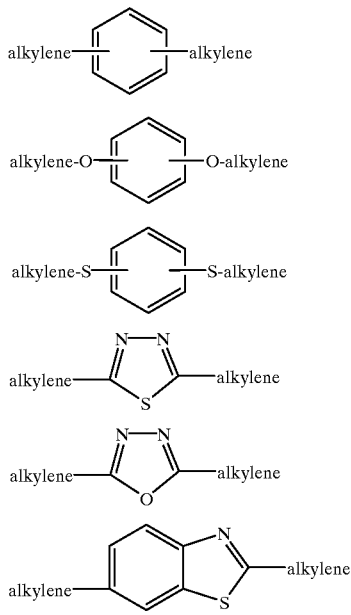

The cycloalkylene groups in the definition of R₁ are typically groups such as 1,2-; 1,3-; and 1,4-cyclohexylene. The carbocyclic arylene groups in the definition of R₁ include typically 1,2-; 1,3-; and 1,4-phenylene and 1,4-; 1,5-; 1,8-; 2,6-; and 2,7-naphthalenediyl and these substituted with one or more groups selected from $C_1$–$C_{12}$ alkyl, $C_1$–$C_{12}$ alkoxy and halogen.

Examples of the divalent heterocyclic arylene groups include unsubstituted and substituted triazines such as 1,3, 5-triazin-2,4-diyl-, 6-methoxy-1,3,5-triazin-2,4-diyl; diazines such as 2,4-pyrimidindiyl, 6-methyl-2,4-pyrimidindiyl, 6-phenyl-2,4-pyrimidindiyl, 3,6-pyridazindiyl and 2-methyl-3-oxo-4,5-pyrazindiyl; dicyano pyridines such as 3,5-dicyano-2,6-pyridindiyl; quinolines and isoquinolines such as 2,4-quinolindiyl and 2,8-isoquinolinediyl; quinoxalines such as 2,3-quinoxalindiyl; azoles such as 2,5-thiazoldiyl, 5-methylene-2-thiazolyl, 3,5- isothiazoldiyl, 5-methylene-3-isothiazolyl, 1,3,4-thiadiazol-2,5-diyl, 1,2,4-thiadiazol-3,5-diyl, 2,6-benzothiazoldiyl, 2,5-benoxazoldiyl, 2,6-benzimidazoldiyl, 6-methylene-2-benzothiazolyl and the group having the formula:

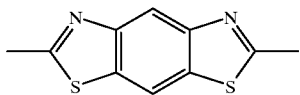

and maleimides such as 1-methyl-3,4-maleimidyl and 1-phenyl-3,4-maleimidediyl.

In addition to the possible substitution described above, the nitrogen atom of the nitrogen containing alkylene groups may be substituted, for example, with $C_1-C_8$ alkyl, aryl, $C_1-C_8$ alkanoyl, aroyl, $C_1-C_8$ alkylsulfonyl or carbamoyl, e.g.

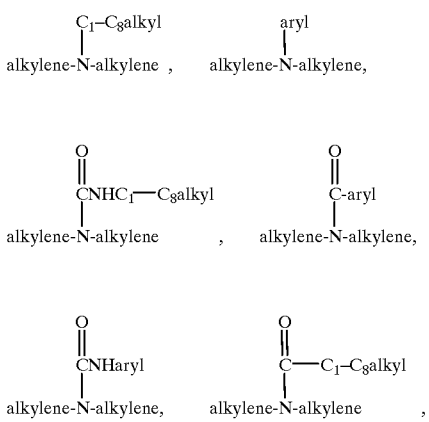

The term "alkylene" is used herein to represent straight or branched chain divalent hydrocarbon moieties having 1–8 carbons which may be further substituted by $C_1-C_8$ alkoxy, $C_1-C_8$ alkanoyloxy, aroyloxy, or halogen. The term $C_3-C_8$ cycloalkylene is used to represent divalent cycloalkylene radicals containing from 3–8, preferably 5 or 6, ring carbons and which may be further substituted by $C_1-C_8$ alkyl or halogen.

The term "$C_1-C_8$ alkyl" is used to describe a monovalent straight or branched chain hydrocarbon radical which may be further substituted by one or more groups selected from $C_1-C_8$ alkoxy, $C_3-C_8$ cycloalkyl, cyano, aryl, heteroaryl, $C_1-C_8$ alkanoyloxy, aroyloxy, and halogen. The term "$C_3-C_8$ cycloalkyl" is used to describe cycloaliphatic hydrocarbon radicals containing three to eight carbon atoms and these optionally substituted with $C_1-C_8$ alkyl, halogen, hydroxymethyl or $C_1-C_8$ alkanoyloxy methyl.

The term "halogen" is used to include fluorine, chlorine, bromine, and iodine. The terms "aryl" and "aroyl" are used herein to describe a group wherein the aromatic portion is a phenyl or naphthyl radical, optionally substituted with one to four groups selected from $C_1-C_8$ alkyl, $C_1-C_8$ alkoxy, $C_1-C_8$ alkylthio, $C_3-C_8$ cycloalkyl, halogen, carboxy, $C_1-C_8$ alkoxycarbonyl, $C_1-C_8$ alkanoylamino, benzoylamino, $C_1-C_8$ alkylsulfonamido, and benzenesulfonamido. The benzoyl and benzene radicals of benzoylamino and benzenesulfonamide may be further substituted by one or more groups selected from $C_1-C_8$ alkyl, $C_1-C_8$ alkoxy, and halogen, respectively. The term "heteroaryl" is used herein to represent mono or bicyclic hetero aromatic radicals containing at least one "hetero" atom selected from oxygen, sulfur, and nitrogen, or a combination of these atoms in combination with carbon to complete the aromatic ring. Examples of suitable heteroaryl groups include: thiazolyl, quinolinyl, benzothiazolyl, pyrazolyl, pyrrolyl, thienyl, furyl, thiadiazolyl, oxadiazolyl, benzoxazolyl, benzimidazolyl, pyridyl, pyrimidinyl, and triazolyl and such groups substituted 1–3 times with a group which may be the same or different and is selected from halogen, $C_1-C_8$ alkyl, $C_1-C_8$ alkylthio, $C_1-C_8$ alkoxy, $C_1-C_8$ alkoxycarbonyl, $C_1-C_8$ alkanoyl-amino, aroylamino, $C_1-C_8$ alkylsulfonamido, or arylsulfonamido. The term "arylene" as used herein preferably denotes divalent benzene and naphthalene radicals and these optionally substituted by one or more groups which may be the same or different and are selected from $C_1-C_8$ alkyl, $C_1-C_8$ alkoxy, $C_1-C_8$ alkylthio, halogen, and $C_1-C_8$ alkoxycarbonyl. The preferred arylene groups are 1,2-; 1,3-; and 1,4-phenylene. In the terms "$C_1-C_8$ alkoxycarbonyl", "$C_1-C_8$ alkanoyl", "$C_1-C_8$ alkanoyloxy", "$C_1-C_8$ alkanoylamino", "$C_1-C_8$ alkoxy", "$C_1-C_8$ alkysulfonyl", "$C_1-C_8$ alkylsulfonamido", "$C_1-C_8$ alkylthio" the alkyl portion of the groups have 1–8 carbons and are straight or branched chain hydrocarbon radicals, optionally substituted with one or more groups listed above as substitutents for the $C_1-C_8$ alkyl radicals. The terms "carbamoyl" and "sulfamoyl" refer to groups of formulae —$CON(R_3)R_4$ and —$SO_2N(R_3)R_4$, respectively, wherein $R_3$ and $R_4$ are independently selected from hydrogen, $C_1-C_8$ alkyl, $C_3-C_8$ cycloalkyl, heteroaryl, and aryl.

The polysulfonamide colorants described above are useful for coloring a variety of thermoplastics such as polyesters; particularly poly(ethylene terephthalate); polyamides, particularly nylon 6 and nylon 66; polyolefins, particularly polyethylene and polypropylene; polyimides, polyesteramides and polystyrene. The polysulfonamide colorants can serve as toners when added at low levels and to impart light to heavy depths of color when added at higher levels. Normally, when serving as toners, e.g. to neutralize yellowness inherent in the production of polyesters, the polysulfonamide colorants are added at about 0.5 to about 15 ppm, preferably at 1–8 ppm. When used as colorants, the polysulfonamide colorants are usually added to the thermoplastics at levels of 0.001–10% by weight, preferably at 0.01–5% by weight. The thermoplastic resins containing the polysulfonamide colorants are useful for a variety of end uses where nonextracting or nonmigrating colorant are needed such as for thick and thin plastic films, plastic sheeting, molded plastic articles and fibers. They have the advantage over pigments of being soluble, thus producing transparent plastic compositions as do currently used solvent dyes, but without the accompanying problems of sublimation, extraction, migration, and exudation.

Compared to the polyester color concentrates mentioned in the prior art which require prolonged times at high temperature (>250° C.) and continuous processing to be cost effective, the polysulfonamide colorants of this invention are prepared at relatively low temperatures and by processes which are adaptable to batch processing. The polysulfonamides of Formula I are prepared by the following general route:

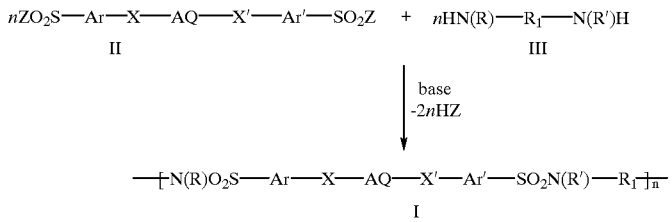

wherein Ar, Ar', X, X', AQ, R, R', R$_1$, and n are as previously defined and Z is fluoro, chloro, or bromo, preferably chloro. The dihalosulfonyl colorant compounds II, containing the anthraquinone chromophore, are reacted with diamines III in a solvent in the presence of an acid acceptor to yield the polysulfonamides of Formula I. The compounds of the formula II wherein Z is fluorine are not known in the art and are particularly useful since they are especially stable to hydrolysis but will still react with the diamine. Normally, the amide producing reactions are carried out at from about 25° C. up to 150° C., but usually at about 50° C. up to about 130° C. Suitable solvents are those in which II and III have sufficient solubility at the desired reaction temperature to facilitate reaction and which will not react with II or III, with aprotic solvents such as N,N-dimethylformnamide, N,N-dimethylacetamide, N-methylpyrrolidinone, hexamethylphosphoramide, dimethylsulfoxide and pyridine being particularly useful. Bases such as trialkylamines, e.g. triethylamine and tri-n-butylamine, N-alkylmorpholines, e.g. 4-methylmorpholine, N,N-dialkylpiperazines, e.g. 1,4-dimethylpiperazine, bicyclic nitrogen containing bases having non-hindered electron pairs, such as 1,8-diazabicyclo [5,4,0] unndec-7-ene (DBU) and 1,4-diazadicyclo [2,2,2,] octane (DABCO®, and alkali metal carbonates and bicarbonates, e.g. potassium carbonate are useful as acid acceptors to facilitate the polycondensation reaction.

Polysulfonamide colorants I may vary considerably in weight average molecular weight and still be useful; however, it is usually desirable that a weight average molecular weight of at least 1,500–20,000 be achieved to avoid problems related to extraction, migration, sublimation, etc. in the use of the colorants at high temperatures. If extremely high weight molecular weights are encountered, the polysulfonamides may not dissolve when used to color thermoplastics, thus functioning as pigments instead of dyes. Normally, a weight average molecular weight range is selected which avoids the problems connected with low weight average molecular weights and which will still allow the polysulfonamide colorants to be largely soluble in the thermoplastic substrate.

Typical dihalosulfonylanthraquinone intermediates II which are useful in the practice of the invention are presented in Table I and typical diamines are given in Table II. Any reactant in Table I may be reacted with any diarnine of Table II to produce a polysulfonamide colorant.

TABLE I

Dihalosulfonylanthraquinones

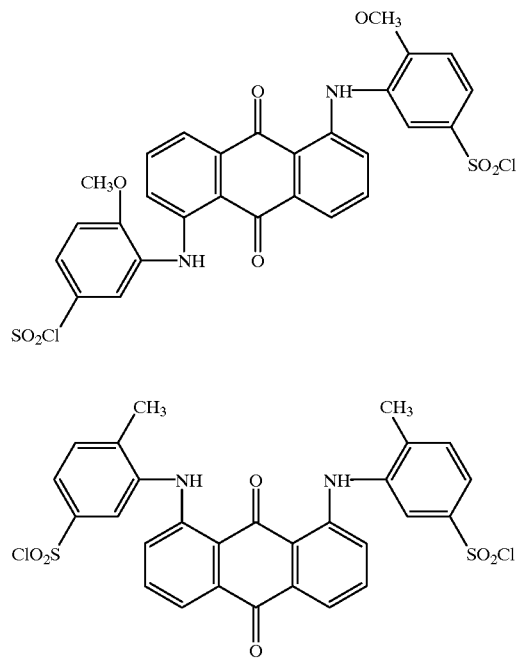

TABLE I-continued
Dihalosulfonylanthraquinones
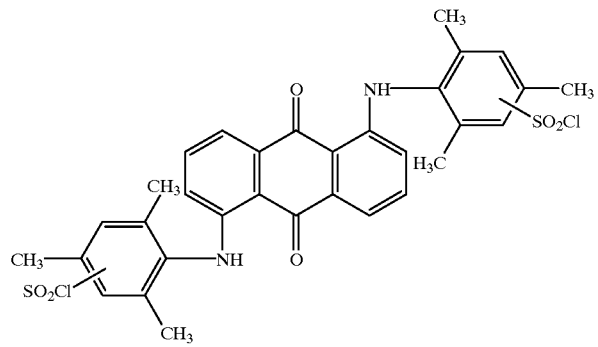
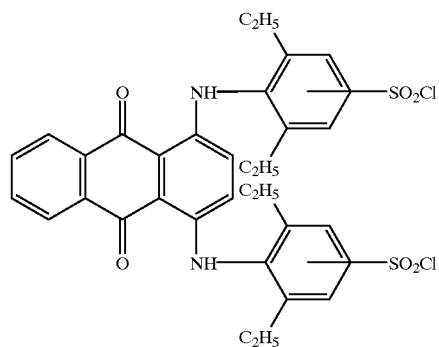
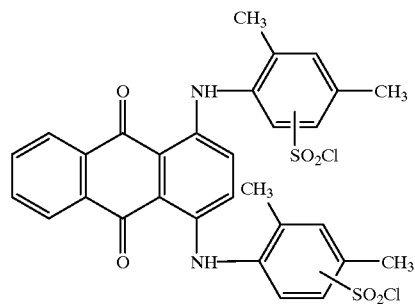
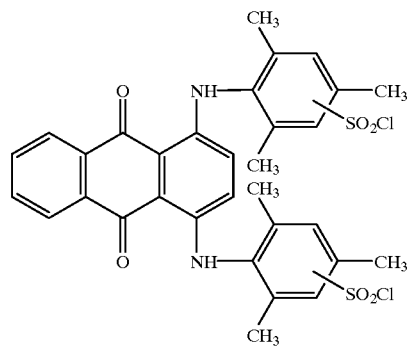

TABLE I-continued
Dihalosulfonylanthraquinones
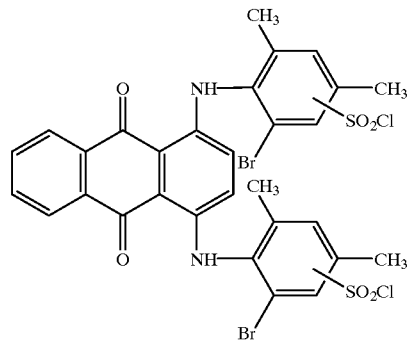
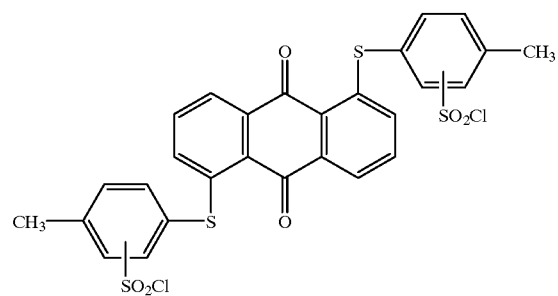
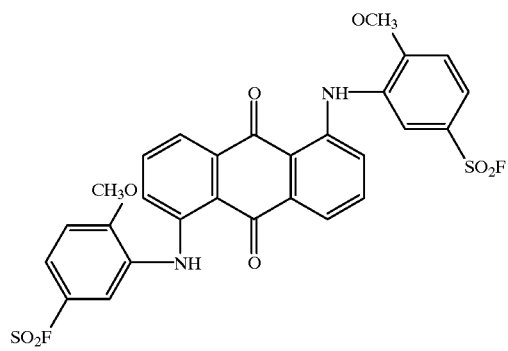
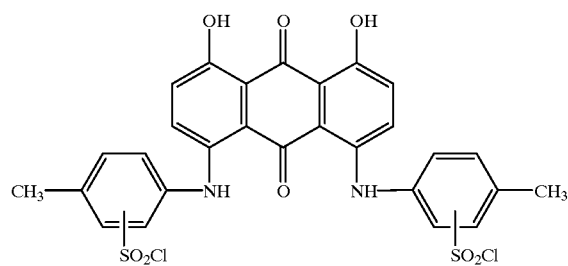

TABLE I-continued
Dihalosulfonylanthraquinones
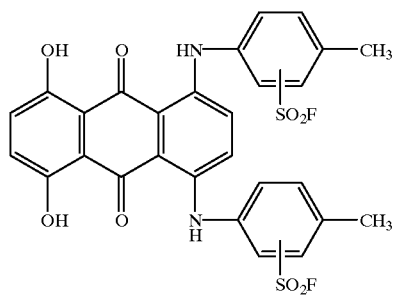
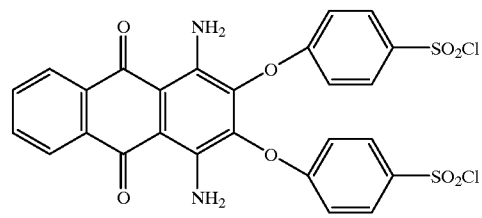
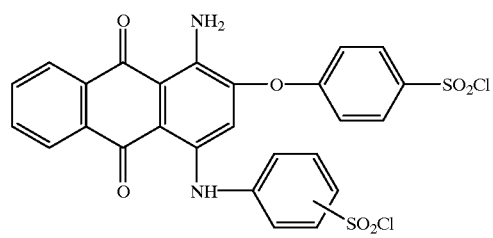
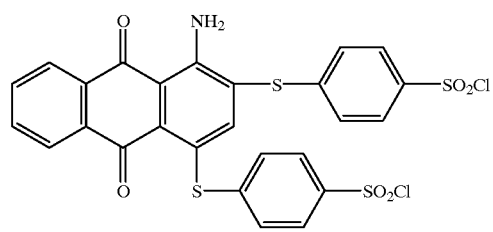
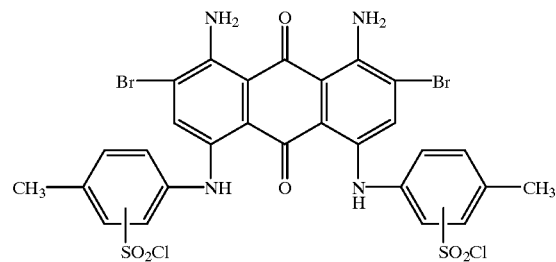
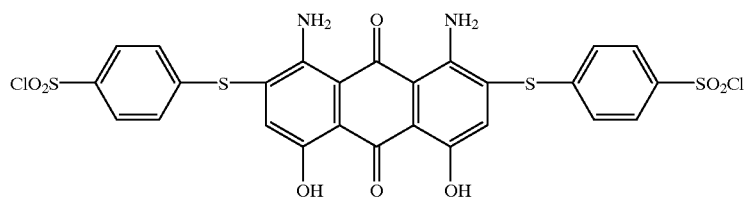

TABLE I-continued
Dihalosulfonylanthraquinones
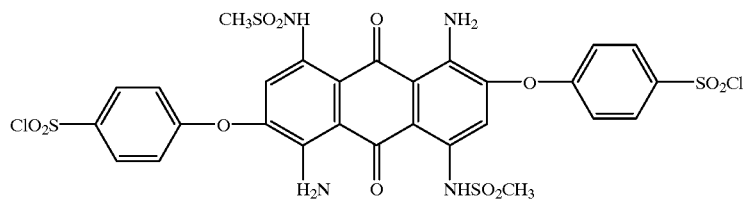
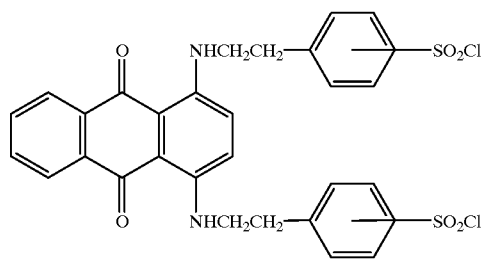
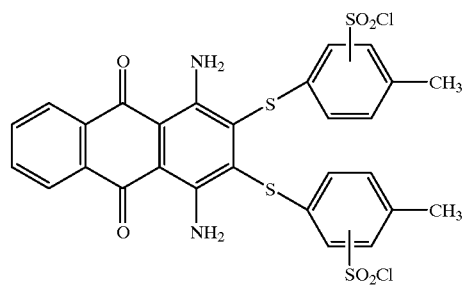
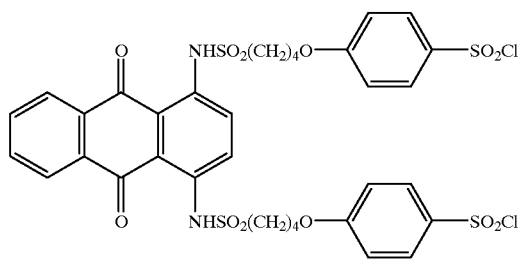
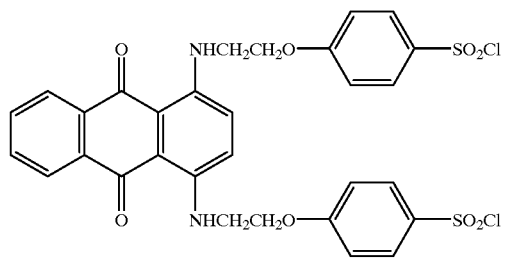

TABLE I-continued
Dihalosulfonylanthraquinones
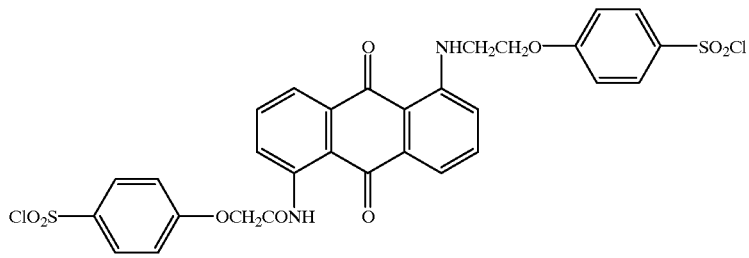
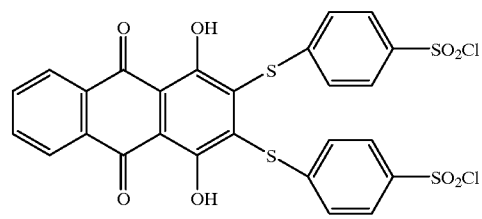
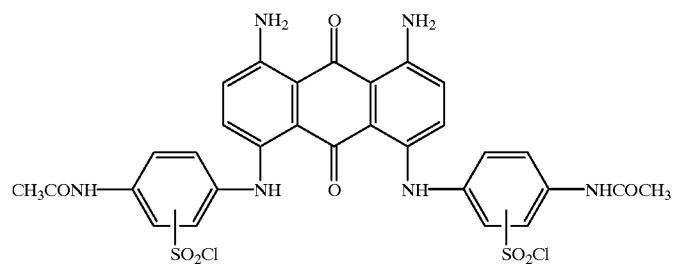
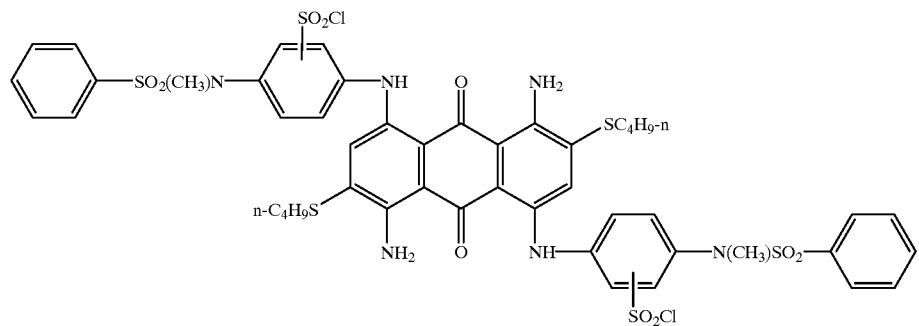
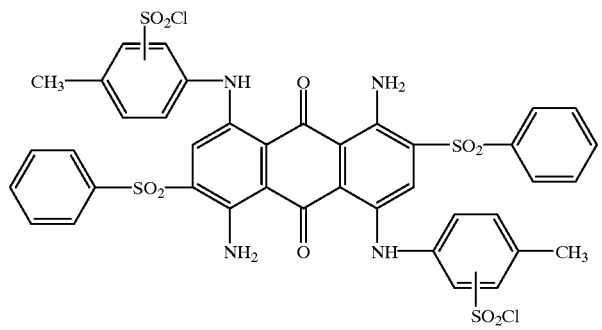

TABLE I-continued
Dihalosulfonylanthraquinones
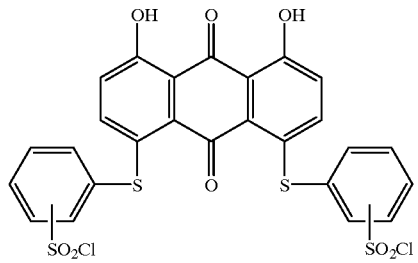
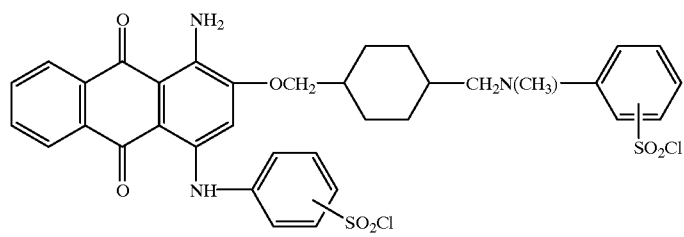
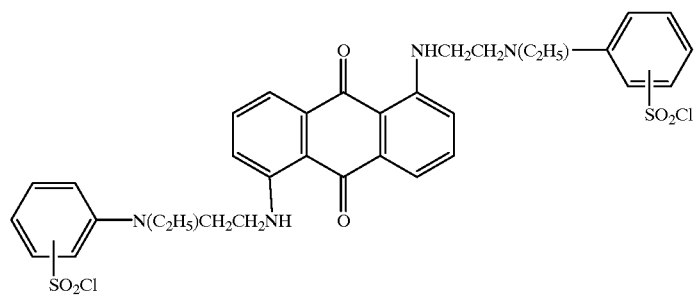
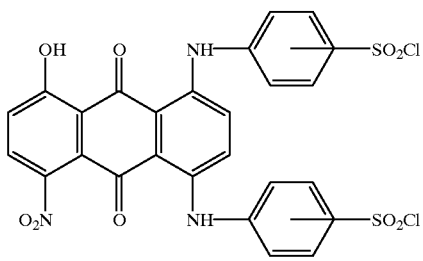
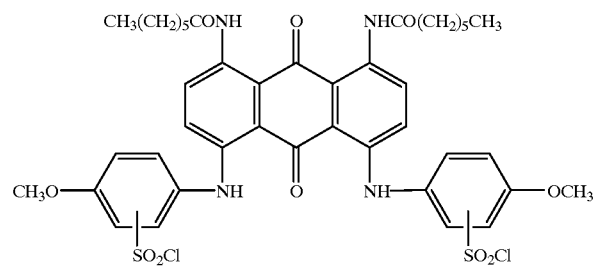

TABLE I-continued
Dihalosulfonylanthraquinones
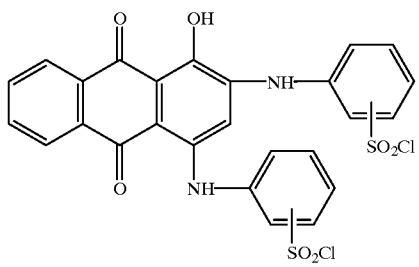
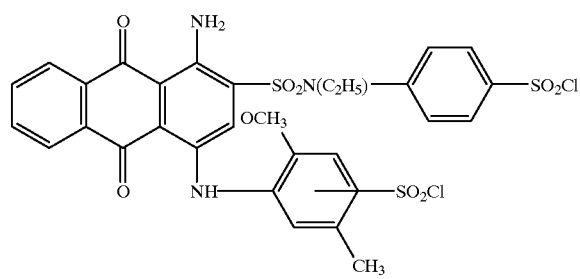
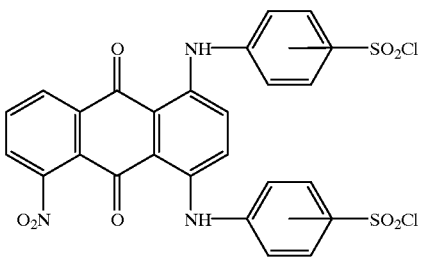
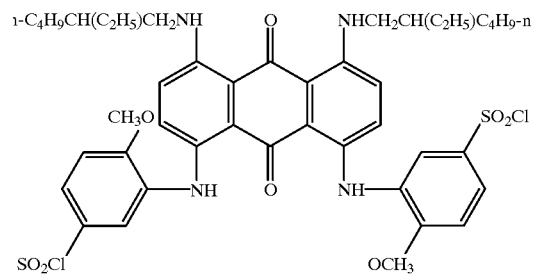
TABLE II
Diamines
$H_2N(CH_2)_{n_1}NH_2$
$H_2N(C_2H_4O)_{n_2}C_2H_4NH_2$
$n_2 = 2–12$
$n_2 = 1–3$
$H_1NCH_2CH_2-N(CH_3)CH_2CH_2NH_2$
$H_2NCH_2CH_2-N(COCH_3)CH_2CH_2NH_2$
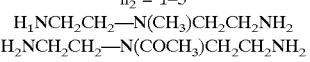
TABLE II-continued
Diamines
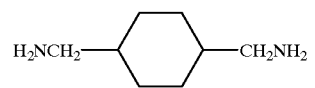
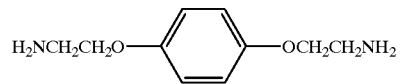

TABLE II-continued

Diamines 1,2-diaminocyclohexane (structure)

HN(CH₃)(CH₂)₆N(CH₃)H
HN(CH₃)(CH₂)₆NH₂

1,3-diaminobenzene (structure)

5-amino-1,3,3-trimethyl-cyclohexanemethanamine (structure)

piperazine (structure)

H₂NCH₂—C(CH₃)₂—CH₂NH₂

H₂NCH₂CH₂—N(C₆H₅)CH₂CH₂NH₂

H₂N—CH₂—C₆H₄—CH₂—NH₂ (para)

H₂NCH₂CH₂N(piperazine)NCH₂CH₂NH₂

HN(CH₃)CH₂CH₂N(CH₃)H 4-aminocyclohexanemethanamine (structure)

1,4-diaminobenzene (structure)

2,4-diamino-1-methylbenzene (structure)

1,2-diaminobenzene (structure)

4,4'-(propane-2,2-diyl)dianiline (structure with CH₃/CH₃)

4,4'-methylenedianiline (structure)

4,4'-ethylenedianiline (structure)

1,3-bis(aminomethyl)cyclohexane (structure)

H₂N(CH₂)₃—N(piperazine)N—(CH₂)₃NH₂

H₂N—C₆H₄—Q—C₆H₄—NH₂

H₂N—C₆H₄—Q—(CH₂)₁₋₆—Q—C₆H₄—NH₂

4,4'-biphenyldiamine (structure)

2,3,5,6-tetramethyl-1,4-phenylenediamine (structure with 4 CH₃)

H₂NCH₂CH₂N(C₆H₅)CH₂CH₂NH₂

H₂N—C₆H₄—Q—(CH₂)₁₋₆—C₆H₄—NH₂

H₂N—C₆H₄—(CH₂)₁₋₆-Q—(CH₂)₁₋₆—C₆H₄—NH₂ wherein Q and Q' are independently selected from —O—, —S—, —SO₂—, —CO—, —CO₂—, —OCO₂—, —CONH—, —NHCONH—, and —NHSO₂—.

If desired, mixed colors may be prepared by selecting more than one colored dihalosulfonylanthraquinone intermediate and reacting with one or more diamines to produce "mixed" colors. For example, yellow, red, and blue, dihalosulfonylanthraquinones may be combined and reacted with the desired diamine to produce a black polysulfonamide colorant. As will be appreciated by those skilled in the art of color technology, a multiplicity of colors may be obtained by combining individual colors, e.g. substractive colors such as yellow, magenta, and cyan (see N. OHTA, Photographic Science and Engineering, Vol. 15, No. 5, September–October 1971, pp. 395–415). In the practice of this invention the individual colorant moieties may be combined at various stages:

a) two or more reactive dihalosulfonylanthraquinone intermediates are reacted with one or more diamines to give a colored polysulfonamide;

b) two or more colored polysulfonamides are combined and then added to thermoplastic materials by known methods.

The dihalosulfonylanthraquinone intermediate compounds II are normally prepared by reacting anthraquinone compounds IV containing two electron rich aryl groups with excess halosulfonic acid, e.g. chlorosulfonic, fluorosulfonic at temperatures at from about −10° C. to about 100° C., according to the following general Route I:

Route I

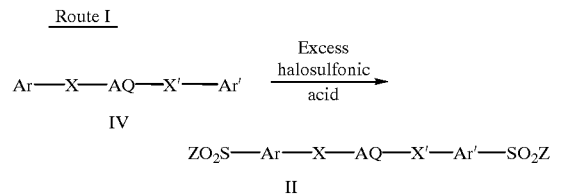

wherein Ar, Ar', X, X', and Z have the meanings ascribed above. Typical procedure for the halosulfonation reactions are described in U.S. Pat. Nos. 2,731,476; 3,299,103; and 4,403,092 and in U.S. Ser. No. 210,785. All of the above mentioned patents and patent applications are incorporated herein by reference. It is also possible to sulfonate IV by contacting with sulfuric acid and/or oleum to produce the disulfonic acid derivatives V.

Route II

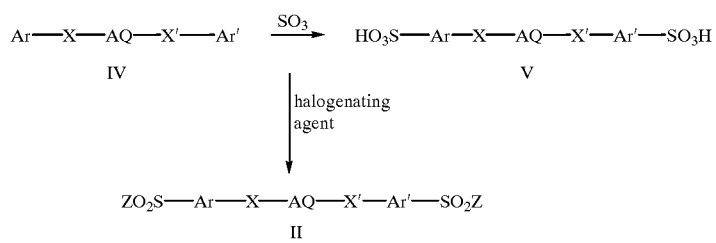

which may be converted into II by using various halogenating agents such as $POCl_3$, $PCl_5$, $PCl_3$, $PBr_3$, $SOCl_2$, $ClSO_3H$, etc. as presented in Route II.

The following examples will illustrate further the practice of the invention. The weight average molecular weights (Mw) and the number average molecular weights (Mn) of the polysulfonamide colorants were determined using gel permeation chromatography (GPC). The glass transition temperatures (Tg) and the melting temperatures (Tm) were determined by differential scanning calorimetry (DSC).

EXAMPLE 1

To chlorosulfonic acid (250 ml) was added 1,5-bis(2-anisidino)anthraquinone (45.0 g, 0.10 m) with stirring at <35° C. After complete addition, the reaction solution was stirred at about 25° C. for 3.0 hours and then added gradually to acetone (4.0 L) with stirring and with external cooling to keep the temperature of the drowning mixture at <20° C. The solid di-sulfonyl chloride compound was collected by filtration, washed well with acetone and dried in air. The yield of product was 56.4 g (87.0% of the theoretical yield). Field desorption mass spectrometry (FDMS) gave a molecular ion mass of 646 from a tetrahydrofuran solution which supports the following desired structure:

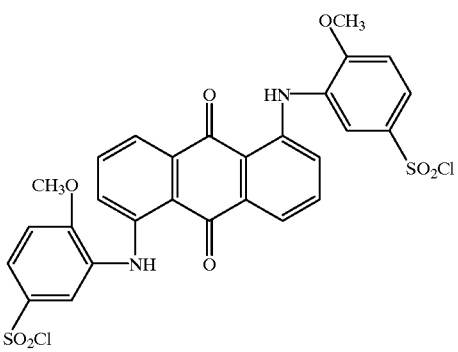

EXAMPLE 2

To chlorosulfonic acid (400 ml) was added 1,4-bis(2,6-diethylanilino)anthraquinone (50.0 g, 0.10 m) portionwise with stirring at <45° C. After being stirred overnight at room temperature, the reaction mixture was added with stirring to acetone (1.0 L), keeping the temperature below about 15° C. The solid thus produced was collected by filtration, washed with acetone (cooled to about 0° C.) and then dried in air. The yield of bright blue product was 47.3 g (67.8% of the theoretical yield). FDMS from a tetrahydrofuran solution of the product showed a molecular ion mass of 698 which supports the following desired structure:

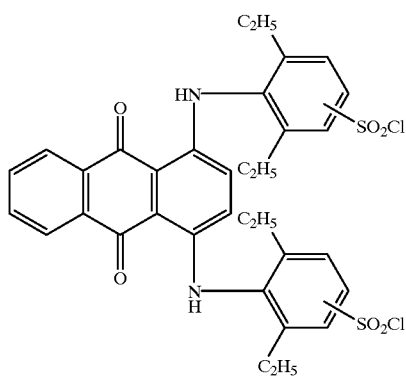

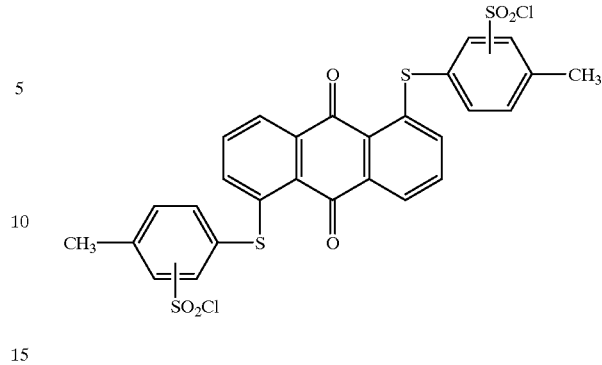

The product was left water-wet and used without further treatment as in Example 19 to prepare a yellow polysulfonamide colorant.

EXAMPLE 3

To fluorosulfonic acid (31.0 ml) was added 1,5-bis(4-tolylthio)anthraquinone (5 g) portionwise with good stirring. After being heated at 95–100° C. for 5 hrs, the reaction mixture was cooled and poured onto an ice/water (500 ml) mixture with stirring. The yellow solid was collected by filtration, washed with cold water and dried in air. The yield of product was 6.3 g (92% of the theoretical yield). FDMS from a DMF solution of the product showed a major molecular ion mass of 616–617 corresponding to the following desired disulfonyl fluoride product:

EXAMPLE 5

To chlorosulfonic acid (200 ml) was added portionwise with good stirring 1,4-bis(2,4-dimethylanilino) anthraquinone (44.6 g, 0.10 m) at 25–50° C. Without any external heating, the reaction mixture was stirred for 2 hrs, allowing the temperature to drop to ambient temperature. The reaction solution was then drowned onto ice/water mixture (2 L) and the blue product was collected by filtration, washed with water, and dried in air (yield—75.0 g). The product was believed to have the following structure:

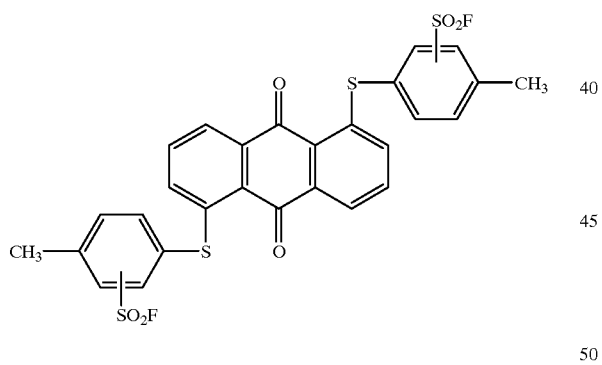

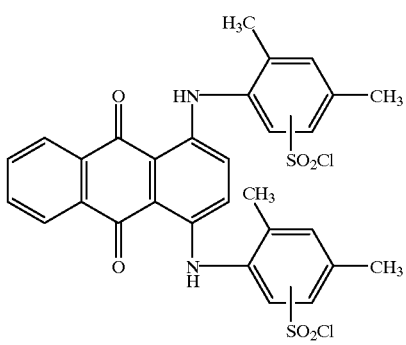

EXAMPLE 4

To chlorosulfonic acid (100 ml) was added portionwise 1,5-bis(4-tolylthio) anthraquinone (18.1 g, 0.04 m) with good stirring allowing the temperature to rise. The reaction mixture was then heated at 75–80° C. for 4 hrs, allowed to stand overnight and then drowned onto an ice/water mixture. The yellow solid which was collected by filtration, washed with water, was believed to have the following structure:

EXAMPLE 6

To chlorosulfonic acid (100 ml) was added portionwise with stirring 1,4-bis(4-toluidino)-5,8-dihydroxyanthraquinone (20.0 g, 0.044 m) allowing temperature to rise. After being heated at about 75° C. for 3 hrs, the reaction mixture was drowned onto an ice/water mixture. The green product was collected by filtration, washed with water, and was believed to have the following structure:

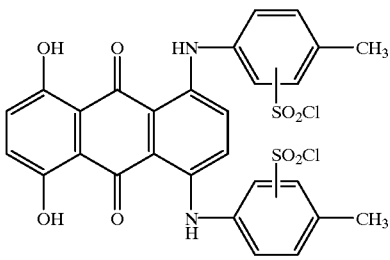

The product was left water-wet and reacted to give a green polysulfonamide colorant as described in Example 18.

EXAMPLE 7

A portion (3.24 g, 0.005 m) of the disulfonyl chloride of Example 1, was added portionwise to a stirred solution of 2,2-dimethyl-1,3-propanediamine (0.51 g, 0.005 m) and tri-n-butylamine (1.85 g, 0.01 m) dissolved in N,N-dimethylformamide (DMF) (20 ml) with good stirring. The reaction mixture was heated at 90–5° C. for 1 hr and then drowned into acetone (200 ml). The red polysulfonamide colorant was collected by filtration, washed with acetone, and dried in air (yield—2.34 g) and had a weight average molecular weight (Mw) of 9,163, a number average molecular (Mn) of 6,946, a polydispersity (Mw/Mn) of 1.32, a glass transition temperature (Tg) at 80° C. and a melting temperature (Tm) at 250° C. An absorption maximum (k max) was observed at 530 nm in the ultraviolet (UV)—visible light absorption spectrum in DMF solution.

EXAMPLE 8

A portion (3.24 g, 0.005 m) of the disulfonyl chloride of Example 1 was reacted with 1,6-hexamethylene diamine (0.58 g, 0.005 m) for 2 hrs and the solid product isolated as described in Example 7 (yield—2.49 g). The red polysulfonamide colorant had a Mw of 8,111, a Mn of 5,236, and a polydispersity (Mw/Mn) of 1.55.

EXAMPLE 9

A portion (3.24 g, 0.005 m) of the disulfonyl chloride of Example 1 was reacted with 1,4-bis(aminomethyl) cyclohexane (0.68 g, 0.005 m) for 1.5 hrs and the solid product isolated as described in Example 7 (yield—2.97 g). The red polysulfonamide colorant had a Mw of 7,058, a Mn of 4,245, and a polydispersity of 1.67.

EXAMPLE 10

A portion (3.24 g, 0.005 m) of the disulfonyl chloride of Example 1 was reacted with N,N'-dimethylhexamethylene diamine (0.72 g, 0.005 m) for 3.5 hrs and the solid polymeric product isolated as described in Example 7 (3.0 g). The red polysulfonamide colorant had a Mw of 10,289, a Mn of 3,937, and a poly-dispersity of 2.61.

EXAMPLE 11

A portion (3.24 g, 0.005 m) of the disulfonyl chloride of Example 1 was reacted with 1,4-phenylene diamine (0.54 g, 0.005 m) for 2.0 hrs and the solid product isolated as described in Example 7. The red polysulfonamide colorant had a Mw of 2,200, a Mn of 1,848, and a polydispersity of 1.19.

EXAMPLE 12

A portion (3.24 g, 0.005 m) of the disulfonyl chloride of Example 1 was reacted with piperazine (0.43 g, 0.005 m) for 4.0 hrs and the solid product isolated as in Example 7. The red polysulfonamide colorant had a Mw of 10,716, a Mn of 4,678, and a polydispersity of 2.29.

EXAMPLE 13

A portion (3.22 g, 0.005 m) of the disulfonyl chloride of Example 5 (3.22 g, 0.005 m) was added portionwise to a solution of 2,2-dimethyl-1,3-propanediamine (0.51 g, 0.005 m) and tri-n-butylamine (1.85 g, 0.01 m) in DMF (20 ml) and the reaction mixture was heated at 90–95° C. for 1.0 hr. The reaction mixture was cooled to room temperature and then drowned into ethanol (200 ml) to precipitate the solid greenish-blue polysulfonamide colorant which was collected by filtration, washed with ethanol, and dried in air (yield—0.75 g). The polysulfonamide colorant had a Mw of 2,540, a Mn of 2,001, a polydispersity of 1.27, a Tg at 80° C. and a Tm at 250° C. In DMF solution, an absorption maximum (λmax) was observed at 631 nm in the UV-visible absorption spectrum.

EXAMPLE 14

A portion of the disulfonyl chloride of Example 2 (3.50 g, 0.005 m) was added portionwise with good stirring to a solution of 2,2-dimethyl-1,3-propanediamine (0.51 g, 0.005 m) and tri-n-butylamine (1.85 g, 0.01 m) in DMF (30 ml) and the reaction mixture was heated at 90–95° C. for 1.0 hr. After cooling, the reaction mixture was drowned into methanol (200 ml) with stirring. The blue polysulfonamide colorant was collected by filtration, washed with methanol, and dried in air (yield—1.85 g) and had a Mw of 6,930, a Mn of 5,145, a polydispersity of 1.35, a Tg of about 80° C. and a melting temperature of about 250° C. In a DMF solution, absorption maxima were observed at 579 and 624 nm in the UV-visible light absorption spectrum.

EXAMPLE 15

A portion of the disulfonyl chloride of Example 2 was added portionwise with good stirring to a solution of hexamethylene diamine (0.58 g, 0.005 m) and tri-n-butylamine (1.85 g, 0.01 m) in N-methyl-2-pyrrolidinone (10.0 ml) and the reaction mixture was heated at 90–95° C. for 4.0 hr. After cooling, the reaction mixture was drowned with stirring into methanol (200 ml). The precipitated blue polysulfonamide colorant was collected by filtration, washed with acetone, and dried in air (0.75 g) and had a Mw of 4,976, a Mn of 1,081, and a polydispersity of 4.60.

EXAMPLE 16

A portion (3.50 g, 0.005 m) of the disulfonyl chloride of Example 2 was added portionwise with good stirring to a solution of piperazine (0.43 g, 0.005 m) and tri-n-butylamine (1.85 g, 0.01 m) dissolved in DMF (20 ml) and the reaction mixture was heated at 90° C. for 3.0 hrs. After cooling to 40° C., the reaction mixture was added to acetone (200 ml) with stirring. The blue polysulfonamide solid colorant which precipitated was collected by filtration, washed with acetone, and dried in air (1.3 g) and had a Mw of 19,858, a Mn of 10,946, and a polydispersity of 1.81.

EXAMPLE 17

A portion (3.50 g, 0.005 m) of the disulfonyl chloride of Example 2 was added portionwise to a solution of N,N'-dimethylhexamethylene diamine (0.72 g, 0.005 m) and tri-n-butylamine (1.85 g, 0.01 m) and the stirred reaction mixture heated for 3.5 hrs at about 95° C. The reaction mixture was cooled and drowned with stirring into methanol (200 ml) to precipitate the blue polysulfonamide colorant which was collected by filtration, washed with methanol, and dried in air (yield 2.5 g) and which had a Mw of 2,828, a Mn of 1,329, and a polydispersity of 2.12.

EXAMPLE 18

One fourth of the water-wet disulfonyl chloride of Example 6 was added with good stirring to a solution of 2,2-dimethyl-1,3-propanediamine (1.02 g, 0.01 Im) and tri-n-butylamine (3.7 g, 0.02 m) dissolved in DMF (80 ml) and the reaction mixture was heated at 90–95° C. for 2.5 hrs. After cooling, the reaction mixture was drowned into methanol (400 ml) with stirring. The green polysulfonamide colorant which was collected by filtration, washed with methanol, and dried in air (yield—3.1 g) had a Mw of 3,308, a Mn of 1,873, and a polydispersity of 1.76.

EXAMPLE 19

One third of the water-wet disulfonyl chloride of Example 4 was added portionwise to a stirred solution of 2,2-dimethyl-1,3-propanediamine (1.35 g, 0.0133 m) and tri-n-butylamine (0.0266 m) dissolved in DMF (60 ml) and the reaction mixture was heated at 90–95° C. for 3.0 hrs. After cooling, the reaction mixture was drowned with stirring into methanol (400 ml) and the product collected by filtration, washed with methanol, and dried in air (yield—5.7 g). The yellow polysulfonamide colorant had a Mw of 3,771, a Mn of 2,471, and a polydispersity of 1.53.

EXAMPLE 20

A portion (2.46 g, 0.004 m) of the yellow disulfonyl chloride of Example 3 was added portionwise with stirring to a solution of 2,2-dimethyl-1,3-propanediamine (0.41 g, 0.004 m) dissolved in DMF (25 g). Sodium bicarbonate (0.67 g, 0.008 m) was added and the reaction mixture was stirred and heated at about 140° C. for 5.5 hrs. After water was added to the cooled reaction mixture to precipitate the yellow polysulfonamide colorant which was collected by filtration, washed with methanol, and dried in air (yield—2.86 g). An absorption maximum ($\lambda$.max) was observed at 445 nm in the UV-visible light absorption spectrum in DMF solvent.

What is claimed is:

1. A polymeric colorant comprising a unit of the formula:

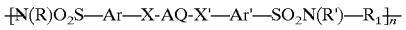

wherein:
AQ is a divalent anthraquinone radical which may be substituted with from 1 to 6 substituents which may be the same or different and are selected from the group consisting of $C_1$–$C_8$ alkyl, $C_1$–$C_8$ alkoxy, $C_1$–$C_8$ alkanolyamino, aroylamino, $C_1$–$C_8$ alkylthio, halogen, amino, nitro, $C_1$–$C_8$ alkylamino, $C_3$–$C_8$ cycloalkylamino, $C_1$–$C_8$ alkanoyl, $C_1$–$C_8$ alkoxycarbonyl, trifluoromethyl, cyano, $C_3$–$C_8$ cycloalkoxy, $C_3$–$C_8$ cycloalkylthio, heteroarylthio, $C_1$–$C_8$ alkylsulfonyl, arylsulfonyl, aroyl, carbamoyl, sulfamoyl, aroylamino, $C_1$–$C_8$ alkylsulfonamido, arylsulfonamido, arylthio, aryloxy, arylamino or hydroxy groups;

X and X' are independently selected from the group consisting of Y, -Y-alkylene, -Y-(alkylene-Y'-)$_m$, -Y-alkylene-$C_3$–$C_8$-cycloalkylene, Y-$C_3$–$C_8$-cycloalkylene-Y', and Y-alkylene-$C_3$–$C_8$-cycloalkylene-alkylene-Y', wherein m is 1–3, and Y and Y' are independently —O—, —S—, —N(R)CO—, —N(R)SO$_2$—, or —N(R$_2$)—;

Ar and Ar' are independently a divalent benzene or naphthalene radical which may be substituted with from 1 to 4 $C_1$–$C_8$ alkyl, $C_1$–$C_8$ alkoxy, $C_1$–$C_8$ alkanolyamino, aroylamino, $C_1$–$C_8$ alkylthio or halogen groups;

R and R' are independently hydrogen, $C_1$–$C_8$ alkyl, $C_3$–$C_8$ cycloalkyl, heteroaryl or aryl;

R$_1$ is a divalent organic radical, with the proviso that when R$_1$ is ethylene, R and R' may be combined to represent an ethylene radical;

R$_2$ is selected fom the group consisting of hydrogen, $C_1$–$C_8$ alkyl, $C_3$–$C_8$ cycloalkyl, $C_1$–$C_8$ alkanoyl, aroyl, $C_1$–$C_8$ alkylsulfonyl, arylsulfonyl, carbamoyl, or sulfamoyl; and n is an integer of from about 3 to about 30.

2. The polymeric colorant of claim 1 wherein R$_1$ is selected from the group consisting of $C_2$–$C_{12}$ alkylene, $C_3$–$C_8$ cycloalkylene, carbocyclic or heterocyclic arylene wherein the alkylene group may contain one or more hetero atoms, cyclic groups or ester/amide groups within or attached to its main chain.

3. The polymeric colorant of claim 2 wherein R$_1$ is an alkylene group which contains one or more moieties within or attached to its main chain selected from the group consisting of oxygen, sulfur, or nitrogen atoms, substituted nitrogen, $C_3$–$C_8$ cycloalkylene, carbocyclic arylene, or divalent aromatic heterocyclic groups.

4. A process for preparing a polymeric colorant of the formula:

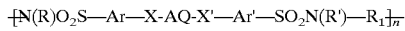

wherein:
AQ is a divalent anthraquinone radical which may be substituted with from 1 to 6 substituents which may be the same or different and are selected from the group consisting of $C_1$–$C_8$ alkyl, $C_1$–$C_8$ alkoxy, $C_1$–$C_8$ alkanolyamino, aroylamino, $C_1$–$C_8$ alkylthio, halogen, amino, nitro, $C_1$–$C_8$ alkylamino, $C_3$–$C_8$ cycloalkylamino, $C_1$–$C_8$ alkanoyl, $C_1$–$C_8$ alkoxycarbonyl, trifluoromethyl, cyano, $C_3$–$C_8$ cycloalkoxy, $C_3$–$C_8$ cycloalkylthio, heteroarylthio, $C_1$–$C_8$ alkylsulfonyl, arylsulfonyl, aroyl, carbamoyl, sulfamoyl, aroylamino, $C_1$–$C_8$ alkylsulfonamido, arylsulfonamido, arylthio, aryloxy, arylamino, and hydroxy groups;

X and X' are independently selected from the group consisting of Y, -Y-alkylene, -Y-(alkylene-Y'-)$_m$, -Y-alkylene-$C_3$–$C_8$-cycloalkylene, Y-$C_3$–$C_8$-cycloalkylene-Y', or Y-alkylene-$C_3$–$C_8$-cycloalkylene-alkylene-Y', wherein m is 1–3, and Y and Y' are independently —O—, —S—, —N(R)CO—, —N(R)SO$_2$—, or —N(R$_2$)—;

Ar and Ar' are independently a divalent benzene or naphthalene radical which may be substituted with from 1 to 4 substituents selected from the group consisting of $C_1$–$C_8$ alkyl, $C_1$–$C_8$ alkoxy, $C_1$–$C_8$ alkanolyamino, aroylamino, $C_1$–$C_8$ alkylthio or halogen groups;

R and R' are hydrogen, $C_1$–$C_8$ alkyl, $C_3$–$C_8$ cycloalkyl, heteroaryl or aryl;

R$_1$ is a divalent organic radical, with the proviso that when R$_1$ is ethylene, R and R' may be combined to represent an ethylene radical;

R$_2$ is selected from the group consisting of hydrogen, $C_1$–$C_8$ alkyl, $C_3$–$C_8$ cycloalkyl, $C_1$–$C_8$ alkanoyl, aroyl, $C_1$–$C_8$ alkylsulfonyl, arylsulfonyl, carbamoyl, or sulfamoyl; and n is an integer of from about 3 to about 30, which comprises reacting at least one dihalosulfonyl compound of the formula:

ZO$_2$S—Ar—X-AQ-X'—Ar'—SO$_2$Z with at least one diamine of the formula HN(R)—R$_1$—N(R')H, in a solvent which does not react with the dihalosulfonyl compound or the diamine, and in the presence of an acid acceptor, wherein Z is a halogen.

5. The process of claim 4 wherein Z is fluorine, chlorine or bromine.

6. The process of claim 4 wherein the acid acceptor is a base.

7. The process of claim 4 wherein the acid acceptor is a base selected from the group consisting of trialkylamines, N-alkylmorpholines, N,N-dialkylpiperazines, and alkali metal carbonates, bicarbonates and bicyclic nitrogen bases containing non-hindered electron pairs.

8. The process of claim 4 wherein the solvent is an aprotic solvent selected from the group consisting of N,N-dimethylformamide, N,N-dimethylacetamide, N-methylpyrrolidinone, hexamethylphosphoramide, dimethylsulfoxide and pyridine.

9. The process of claim 4 wherein the reaction is carried out at a temperature of from about 25° C. to about 150° C.

10. The process of claim 4 wherein R$_1$ is C$_2$–C$_{12}$ alkylene, —CH$_2$—C$_3$—C$_8$ cycloalkylene-CH$_2$—, C$_3$–C$_8$ cycloalkylene, carbocyclic or heterocyclic arylene wherein the alkylene group may contain one or more hetero atoms, cyclic groups or ester/amide groups within or attached to its main chain.

11. The process of claim 5 wherein R$_1$ is an alkylene group which contains one or more oxygen, sulfur, or nitrogen atoms, substituted nitrogen, C$_3$–C$_8$ cycloalkylene, carbocyclic arylene, or divalent aromatic heterocyclic groups within or attached to its main chain.

12. The process of claim 4 wherein the reaction is conducted by reacting more than one dihalosulfonyl compound of the formula:

ZO$_2$S—Ar—X-AQ-X'—Ar'—SO$_2$Z.

13. The process of claim 4 wherein the reaction is conducted by reacting more than one diamine of the formula HN(R)—R$_1$—N(R')H.

14. The process of claim 4 wherein the reaction is conducted by reacting more than one dihalosulfonyl compound of the formula:

ZO$_2$S—Ar—X-AQ-X'—Ar'—SO$_2$Z with at least one diamine of the formula HN(R)—R$_1$—N(R')H.

15. A colored composition comprising the polymeric colorant of claim 1.

16. The colored composition of claim 15 which is a cream, a lotion, a polish, a wax, a hair coloring, a paint or an ink.

* * * * *